United States Patent [19]

Bernath

[11] 4,342,234

[45] Aug. 3, 1982

[54] APPARATUS FOR EXTRACTING A HOT GAS SAMPLE FROM A CHAMBER AND FOR FEEDING THE SAMPLE TO AN ANALYZER

[76] Inventor: Tibor Bernath, Hauptstrasse 48, D-3000 Hannover 91, Fed. Rep. of Germany

[21] Appl. No.: 216,648

[22] Filed: Dec. 15, 1980

[30] Foreign Application Priority Data

Dec. 17, 1979 [DE] Fed. Rep. of Germany ....... 2950744

[51] Int. Cl.³ .............................................. G01N 1/22
[52] U.S. Cl. ................................................ 73/863.12
[58] Field of Search ........... 73/863.11, 863.12, 864.81, 73/864.82; 422/78, 79, 80

[56] References Cited

U.S. PATENT DOCUMENTS

| 3,486,382 | 12/1969 | Vivares et al. | 73/863.12 |
| 3,517,557 | 6/1970 | Granger | 73/863.12 |
| 3,586,488 | 6/1971 | Travalion | 73/863.12 |
| 4,191,541 | 3/1980 | Jenkins | 73/863.12 |
| 4,289,029 | 9/1981 | Sampson | 73/863.11 |

Primary Examiner—S. Clement Swisher
Attorney, Agent, or Firm—Pennie & Edmonds

[57] ABSTRACT

An apparatus for sampling hot gas from a chamber includes a sample probe surrounded by a heating jacket, leading directly to a heated analyzer. The heating of the analyzer and the probe is separately controlled. A filter is provided within the probe.

5 Claims, 4 Drawing Figures

APPARATUS FOR EXTRACTING A HOT GAS SAMPLE FROM A CHAMBER AND FOR FEEDING THE SAMPLE TO AN ANALYZER

BACKGROUND OF THE INVENTION

The present invention relates to an apparatus for extracting a hot gas sample from a chamber and for feeding the sample to an analyzer, in particular for monitoring the content of organic solvents or similar constituents in the air in the chamber, which such solvents or similar constituents represent an explosion hazard or are otherwise harmful when they reach a specific concentration, such apparatus comprising a sampling probe which can be introduced into the chamber through an opening in the chamber wall and is connected outside the chamber with the analyzer, which has a gas filter and a detector, there being a suction pump to draw off the sample through the probe to the analyzer, as well as a heating jacket upstream of the analyzer.

Such apparatus is already known, in which the rear end of the probe is connected outside the chamber via a flexible hose with the analyzer, which is located at least 5 to 30 meters away from the site where the sampling probe passes through the chamber wall. The heating jacket surrounds the hose connecting the probe with the analyzer.

In this known configuration, it is a disadvantage that the gas sample cannot be prevented from cooling down, despite the heating jacket, on its way from the chamber to the analyzer, resulting in the condensation of such constituents in the sample as saturate or nearly saturate the air in the chamber. This condensation which takes place upstream of the analyzer leads to the analyzer results not reflecting the actual conditions in the chamber, so that an existing explosion hazard may not be recorded and taken into account. In addition, the deposit of condensate may even lead to the passage for the gas sample becoming blocked, so that measurements cease altogether. The heating jacket provided for the connecting hose can counteract these hazards only to a limited extent. The temperature of the gas sample first drops in the zone of the passage through the chamber wall. Particularly the screw couplings for joining the connecting hose to the sampling probe, on the one hand, and to the analyzer, on the other hand, constitute cold sites, however, where there is an enhanced risk of condensation. This is especially so, when the temperature in the chamber, and thus of the gas sample, is high at 250° C. or more, a temperature drop of some 80° C. having been recorded at the cold sites. Under such conditions, substantial condensation of constituents with a high boiling point can be reckoned with in the sample.

Another disadvantage of the known configuration is the time lag with which the analyzer records changes in concentration inside the chamber. If the suction pump has a normal throughput of 3 l/min and the internal diameter of the hose connecting the sampling probe with the analyzer is 4 mm, the retention time is approx. 2.4 secs per meter of the connecting hose. For a connecting hose 15 meters long, for instance, the time lag in the measurements is as much as 36 secs. something which is unacceptable in monitoring a process involving an explosion hazard.

From U.S. Pat. No. 2,648,976 of Bur, a method is known of connecting a gas sampling tube by a short flexible conduit to an analyzer, the flexible conduit serving to make it possible to shift the receiving end of the sampling tube extending into the chamber through which gas to be sampled is passing, in order to withdraw gas samples at points over the cross section of the chamber, the angular length of tube inside the chamber being moved to and fro within an arc for this purpose and also being shiftable axially. In this case, however, the analysis of furnace gases is involved, heating or insulating apparatus being employed neither with the sampling tube nor with the flexible conduit nor with the analyzer. For this reason, the withdrawn gas sample suffers a considerable drop in temperature in this case too, despite the analyzer being not far away from the chamber, so that condensation must likewise be reckoned with and accordingly distorted sampling analysis when the gas sample has an appropriate composition.

From the U.S. Pat. No. 3,793,887 of Anderson et al., a method is also known, in testing the exhaust of internal combustion engines, of extracting a gas sample by means of a probe introduced into the exhaust duct, the probe being connected to an expandable collection bag for the sample, the bag being in an enclosure and there being separate heating apparatuses for the probe and for the enclosure. This known system serves, however, solely to obtain a gas sample representative of actual conditions over a fairly long running time for the engine, a pump being intended to maintain in the collection bag an instantaneous pressure equal to the instantaneous pressure at the exit to the exhaust duct. Consequently, there is no analyzer in the heated enclosure, the exhaust gas sample instead being analyzed outside the heated enclosure after termination of the lengthy period of sample extraction, so that condensation and incorrect analysis figures are involved in this case too, in the event that the extracted gas sample contains vapours. Moreover, there is no insulation for the sampling probe and the heated enclosure.

SUMMARY OF THE INVENTION

It is an object of the present invention to develop an apparatus of the above-mentioned type in such a manner that dependable, undistorted and real-time analysis results are obtained even under unfavourable conditions, so that the apparatus meets all the requirements made on it on safety grounds.

This object is achieved in the invention, in that the analyzer is located directly at the opening in the chamber wall and is directly connected to the sampling probe, that the heating jacket surrounds the sampling probe and extends beyond the chamber wall through the chamber-wall opening up to the analyzer, that the analyzer has a heating apparatus separate from the heating jacket of the sampling probe and that the heating jacket and heating apparatus each has its own temperature sensor for separate heating and temperature control.

Direct connection of the analyzer to the rear end of the sampling probe significantly shortens the flow path of the gas sample from the extraction point in the chamber to the analyzer, thus ensuring rapid response of the apparatus in the interest of real-time analysis data. Moreover, the gas sample flows through no cold sites involving an increased risk of condensation on its way to the analyzer. Additionally, uninterrupted heating and temperature control along the entire flow path of the gas sample, including the opening through the chamber wall, effectively counteracts even the slightest still harmful drop in temperature, the separate heating of the sampling probe, on the one hand, and of the analyzer, on the other hand, creating optimum conditions for keeping the temperature of the gas sample constant from extraction until analysis.

Expediently, the heating apparatus of the analyzer is provided with an insulating jacket, which holds the adjacent end of a probe insulating jacket surrounding the heating jacket of the sampling probe. In this way, the direct connection between the probe and the analyzer is utilized to create an uninterrupted insulation, without a one-piece overall insulation handicapping assembly and, particularly later-on, accessibility having to be provided.

In an advantageous embodiment of the invention, the heating jacket of the sampling probe and the heating apparatus of the analyzer consist in each case of a metal sleeve with axial bores, into which electrical heating rods and the temperature sensors are inserted. This not only facilitates assembly, checking and exchange of the relevant components but results specifically in a compact apparatus embracing the analyzer, the arrangement of this apparatus on the exterior of the chamber wall following the elimination of the connecting line being a matter which involves no problems even when conditions are unfavourable.

It is also beneficial if the heating jacket for the sampling probe features a radial attachment plate at its end adjacent to the analyzer, such an attachment plate being detachably connected with the analyzer. In this manner, the sampling probe with its surrounding jacket and the analyzer can be easily taken apart for subsequent inspection or for exchanging components, while nevertheless being rigidly connected, a favourable factor for arranging and supporting the apparatus on the exterior of the chamber wall.

In an expedient development, a mug-shaped casing is provided to accommodate the analyzer, the bottom of which casing has a central hole, through which the sampling probe with its surrounding jacket is passed when the analyzer is fitted axially into the casing, and also a projecting flange for attaching it to the chamber wall. Such a casing enables the apparatus to be arranged rapidly and dependably at a suitable site on the chamber wall, the apparatus with its good accessibility nevertheless being protected from external influences, so that in this respect trouble-free functioning of the apparatus can also be relied upon.

The apparatus according to the invention has proved especially suitable for paint shops, strip coating facilities and plant for impregnating wood, fabric or paper, all of which involve vapours or air pollution which become harmful when a certain concentration is reached. However, applications for the apparatus are not limited to these cases.

These and other purposes for the present invention will be evident from the description of the preferred embodiments of the invention read in association with the accompanying drawings.

DESCRIPTION OF THE PREFERRED EMBODIMENTS

Figure 1:
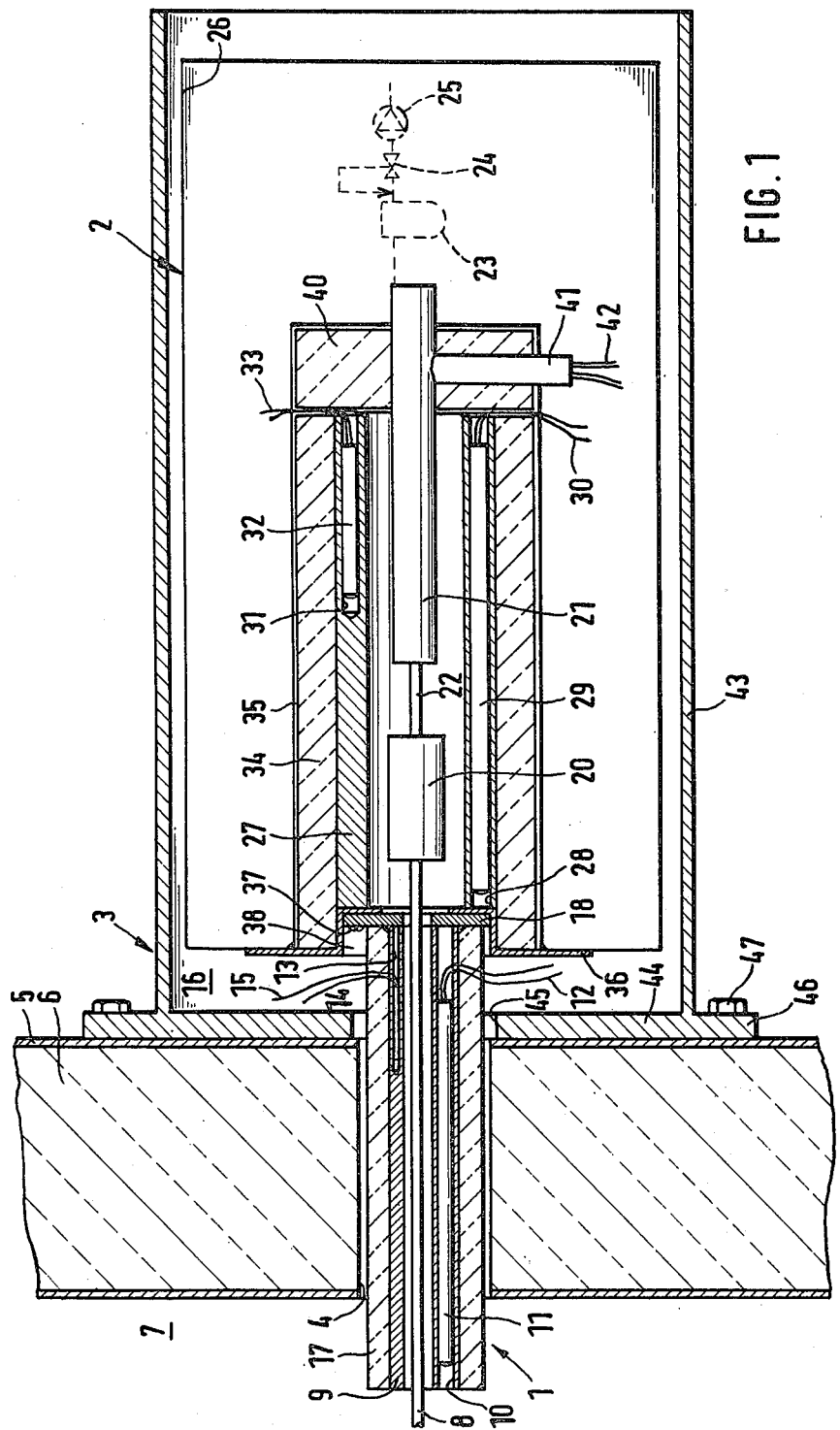
FIG. 1 is a horizontal section through an apparatus according to the invention as attached in service to a chamber wall.

The apparatus comprises mainly a probe head 1, an analyzer 2 and a casing 3, being arranged with the probe head 1 inside an opening 4 through a wall 5 with an insulation 6, said wall enclosing a chamber 7. This chamber 7 may be, for instance, the chamber of a drying stove for an industrial paint shop. When the drying stove is in operation, the chamber 7 contains hot air which carries a concentration of organic solvent vapours. The content of solvent vapours or overall hydrocarbons is continuously determined and monitored by means of the analyzer 2, in order to shut down the facility immediately the concentration rises above an acceptable level.

The probe head 1 includes a centrally sited sampling probe 8, the front end of which sticks out from the wall 5 into the chamber 7. A heating jacket 9 in the form of a metal sleeve surrounds the sampling probe 8 in an intermediate zone, said heating jacket likewise extending through the opening 4 and projecting somewhat beyond the insulated wall 5 at both ends. The heating jacket 9 has axial bores 10 spaced around the circumference, into each of which an electrical heating rod 11 is fitted, the electrical connecting wires 12 for which are routed radially outwards out of the heating jacket 9.

There is also an axial blind hole 13 above said probe in the heating jacket 9, which hole accommodates a temperature sensor 14, for which the connecting wires 15 are likewise routed radially outwards into the casing chamber 16. The heating jacket 9 is surrounded by a probe insulating jacket 17, the outer diameter of which is somewhat smaller than the diameter of the opening 4, as shown in the drawing. Additionally, a radial attachment plate 18, through which the rear end of the sampling probe 8 extends, is permanently connected to the rear end of the heating jacket 9.

The analyzer 2 has a gas filter 20, to which the rear end of the sampling probe 8 is connected, as well as a centrally located detector 21, which is linked by means of a short connecting line 22 with the gas filter 20. Downstream of the detector for the gas sample extracted from the chamber 7 condensation is not harmful, so that parts further downstream need not be heated and have no special significance in the invention. Thus, a collecting vessel 23 for condensate, a vacuum flow controller 24 to ensure a constant flow of the gas sample and a vacuum pump 25 in the form of a diaphragm pump, through all of which the extracted gas sample likewise flows and which are located inside a common enclosure 26, are shown only schematically.

The gas filter 20 and the detector 21 are surrounded by a heating apparatus 27, which likewise consists of a metal sleeve with axial bores 28, into each of which an electrical heating rod 29 with electrical connecting wires 30 is pushed, the wires being routed, as shown, radially outwards into the casing chamber 16. Whereas a heating rod 29 is shown in the drawing below the gas filter 20 and the detector 21, a configuration has proved its worth in which two heating rods 29 are provided located diametrically opposite each other at the same level to the side of the gas filter 20 and the detector 21.

There is an axial blind hole 31 above the detector 21 made in the metal sleeve, i.e., heating apparatus 27 from its rear end, which hole accommodates a temperature sensor 32, for which the connecting wires 33, like the electrical connecting wires 30 at the rear end of the heating apparatus 27, are routed radially outwards into the casing chamber 16. The heating apparatus 27 is surrounded by an insulating jacket 34 with an outer jacket 35, both of these jackets projecting axially beyond the front end of the heating apparatus 27. There is a cover plate 36 of appropriate shape covering the front end face of the heating apparatus 27 and of the insulating jacket 34. The attachment plate 18 of the heating jacket 9 is detachably connected with the heating apparatus 27 by means of screws 37 passing through the cover plate 36. An insulating ring 38 closes the annular gap between the probe insulating jacket 17 and the insulating jacket 34.

An insulating cover 40, through which the rear end of the detector 21 passes and which also accommodates a radial stub from the detector, closes the insulating jacket 34 at its rear end. The signal wires 42 from the detector 21 pass out through the radial stub 41.

The casing 3 is mug-shaped and comprises a cylinder wall 43 and a bottom 44 with a central hole 45, through which the probe head 1 is passed. The bottom 44 features a flange 46 projecting radially outwards from the cylinder wall 43, which flange serves to attach the casing 3 by means of bolts 47 securely to the chamber wall 5.

As shown, the cylinder wall 43 of the casing 3 is so dimensioned that it can completely accommodate the analyzer 2 as a component inside the enclosure 26 and support it at its service site.

The electrical connecting wires 12 and 15 are part of a first temperature control circuit, the connecting wires 30 and 33 part of a second temperature control circuit. Just like the signal wires 42 for the analysis data, they are routed to a microprocessor (not shown) for the overall control system.

The mode of operation of the apparatus is described below with reference to FIG. 2 and, in particular, to FIG. 3.

Figure 3:
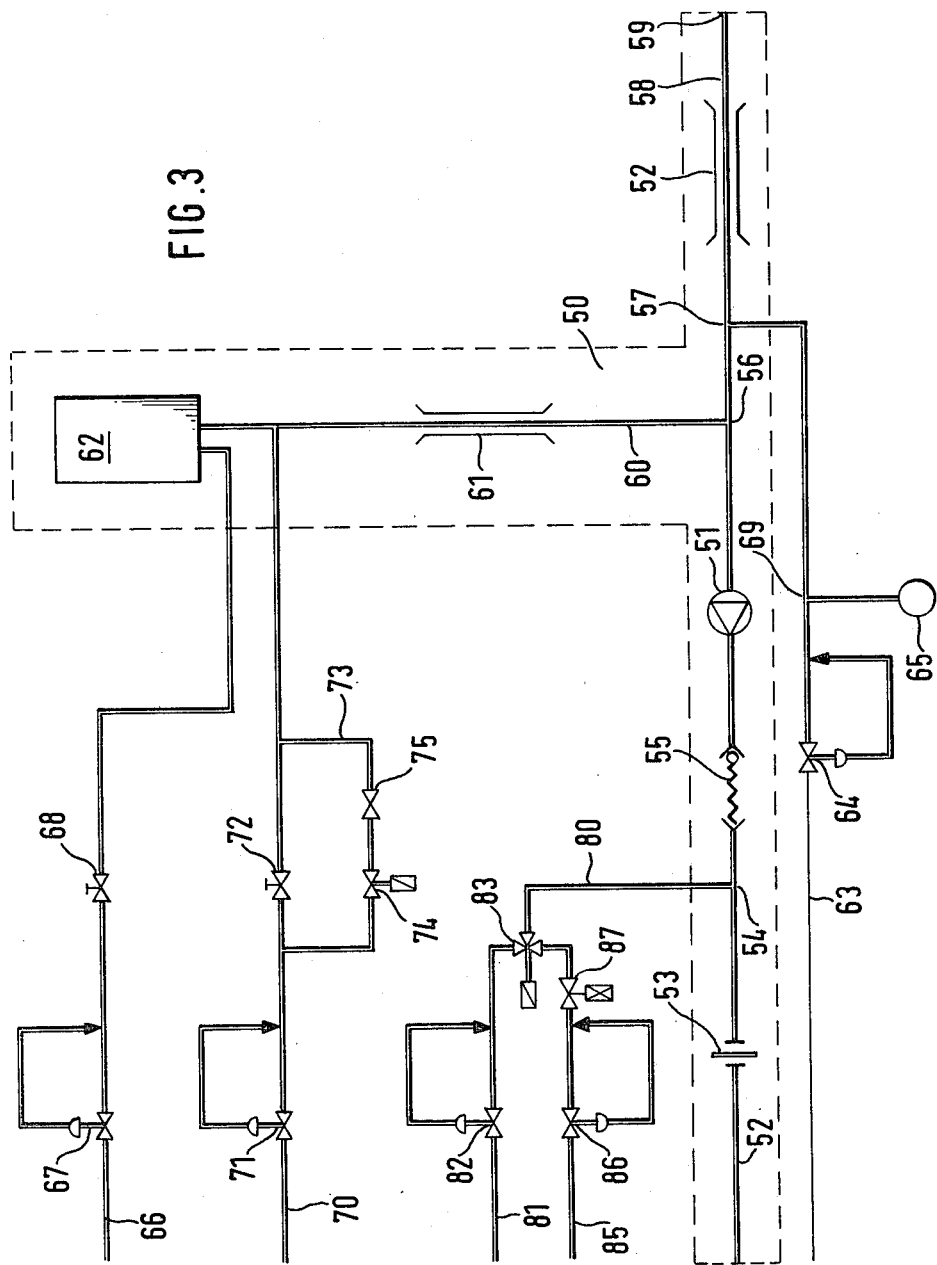
FIG. 3 Flow diagram for the analyzer shown in FIG. 2.

The gas sample to be examined or monitored is caused to flow, as shown in FIG. 3, by the action of a pump 51 integrated in the analysis chamber 50, which is shown by the broken line in the drawing, through a line 52 connected with the sampling probe 8 and thus successively through a gas filter 53, a tee-piece 54, a non-return valve 55, a tee-piece 56, another tee-piece 57, a bypass capillary tube 58 and through the bypass exit 59 of the analysis chamber 50. A branch line 60 with a metering capillary tube 61 is connected to the tee-piece 56, this line leading to a detector 62 arranged in the analysis chamber 50, which detector serves as a flame ionization detector to determine hydrocarbons present in the gas sample.

The gas feed to the detector 62 is determined by the pressure of the gas in the tee-piece 56 and the ambient temperature at the metering capillary tube 61, which temperature is, as was already mentioned, maintained at a constant figure by means of a control device. In order to maintain the inlet pressure constant at the tee-piece 56, a compressed-air line 63 with a pressure regulator 64 and a pressure gauge 65 connected up to a tee-piece 69 is connected with the adjacent tee-piece 57. In this manner, not only some of the gas sample, which has an overpressure of approx. 100 mbar in the tee-piece 56 as a result of the action of the pump 51, but also an extra flow as a function of the setting of the pressure regulator 64 passes through the bypass capillary tube 58. This enables the gas pressure in the tee-piece 56 and in the branch line 60 to be kept at a constant figure.

Combustion air is fed via a line 66 to the detector 62, a feed pressure regulator 67 being employed to obtain a feed pressure of approx. 1 bar. By means of a needle valve 68 the exact combustion air flow rate is set, which is approx. 250 ml/min.

Combustible gas is fed to the detector 62 via a line 70 incorporating a feed pressure regulator 71 and a flow controller 72. The combustible gas feed pressure is regulated to approx. 1 bar, so that the flow controller 72 provides a constant flow rate of combustible gas. When hydrogen is employed as the combustible gas, the maximum flow rate is 30 ml/min. For ignition, the quantity of hydrogen is boosted, for which purpose an ignition gas line 73 incorporating a solenoid valve 74 and a needle valve 75 and bypassing the flow controller 72 is provided. During the ignition cycle, the solenoid valve 74 is opened, so that an extra quantity of combustible gas flows through the needle valve 75 to the detector, which features a not-illustrated platinum ignition coil, this coil being made to glow when an ignition current is switched on to ignite the flame, whereupon the solenoid valve 74 closes again.

A calibration line 80 is connected to the tee-piece 54, which line joins up with a line 81 incorporating a pressure regulator 82 and a solenoid valve 83, as well as with a line 85 incorporating a pressure regulator 86 and a solenoid valve 87.

By means of the calibration gas, which can be fed from a pressure cylinder and for which the exact concentration of hydrocarbons has been determined by gas chromatography, and by means of the zero-hydrocarbon gas it is possible to calibrate the apparatus, which has a linear characteristic enabling two reference points to be employed to determine the working characteristics. The increased output voltage obtained from the detector when calibration gas is fed, provides the signal measuring the value of the calibration-gas concentration. When zero-hydrocarbon gas is fed to determine the signal indicating the absence of hydrocarbons, the pressure regulator 86 is given a setting such that the feed of zero-hydrocarbon gas somewhat exceeds the throughput of the pump 51, resulting in a residual quantity of zero-hydrocarbon gas flowing out through the filter 53 and the sampling probe 8 and excluding a calibration error through the zero-hydrocarbon gas being contaminated with gas from the chamber which has to be monitored.

The described arrangement also affords an adequate safeguard against blowback of the flame from the flame ionization detector 62. This might cause an explosion, if the gas concentration in the monitored chamber were above the lower limit for an explosion. The backfire would have to take place through the metering capillary tube 61, something which experience indicates to be impossible, however, in view of the capillary tube diameter of 0.1 mm and of the flow velocity of 2 m/sec obtained by means of the pump 51 in the opposite direction to the backfire. If the explosion, i.e., backfire nevertheless got through the metering capillary tube 61 to the tee-piece 56, the associated pressure would act to close the valves of the pump 51 if the pressure exceeds the setting of 0.2 bar. As an additional precaution, the non-return valve 55 is fitted. The backfire would also have to pass the filter 53, which features a fine-meshed screen of high-grade steel. It is therefore obvious that the above-mentioned parts are adequate safety measures against a backfire from the flame.

Figure 2:
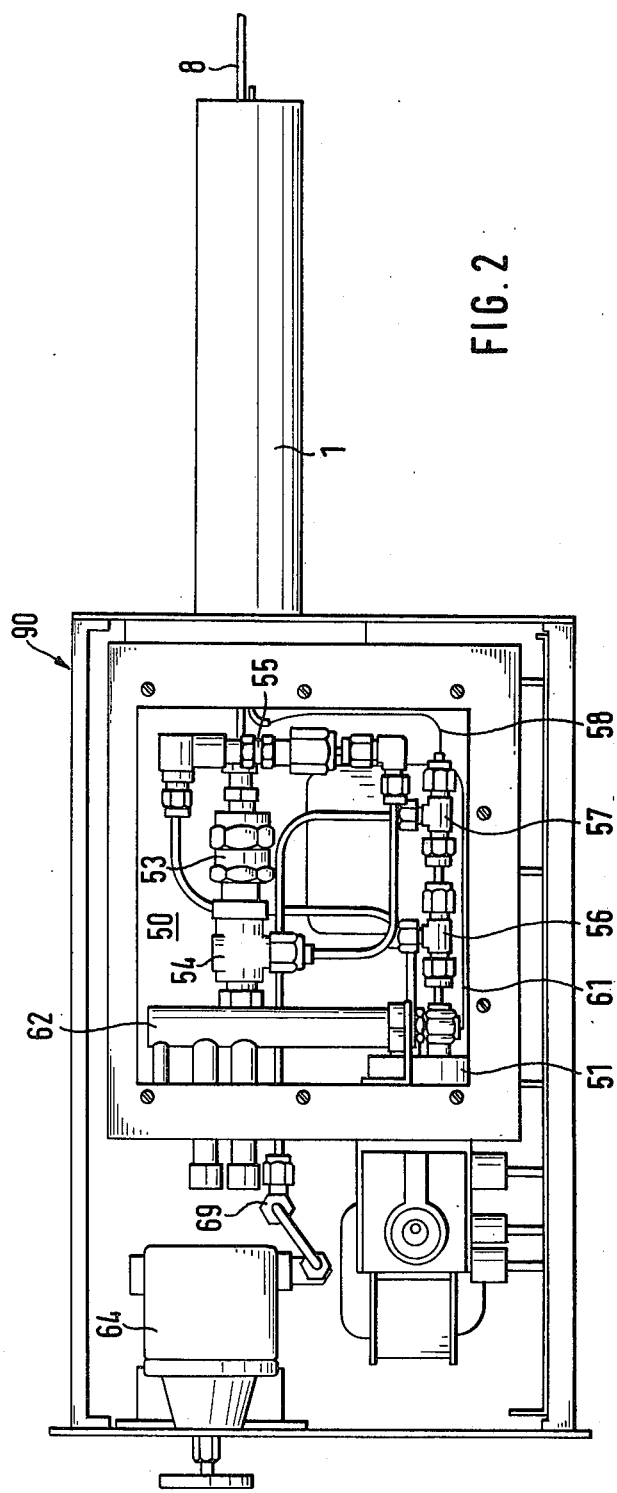
FIG. 2 Side elevation of an analyzer for measuring overall hydrocarbons by means of a flame ionization detector, such an analyzer being employable with an apparatus according to FIG. 1.

FIG. 2 shows for a practical embodiment how the above-mentioned apparatus parts are arranged inside the analysis chamber 50 and combined with the other components to form a compact apparatus within the casing 90, which also carries the probe head 1 with the sampling probe 8.

Figure 4:
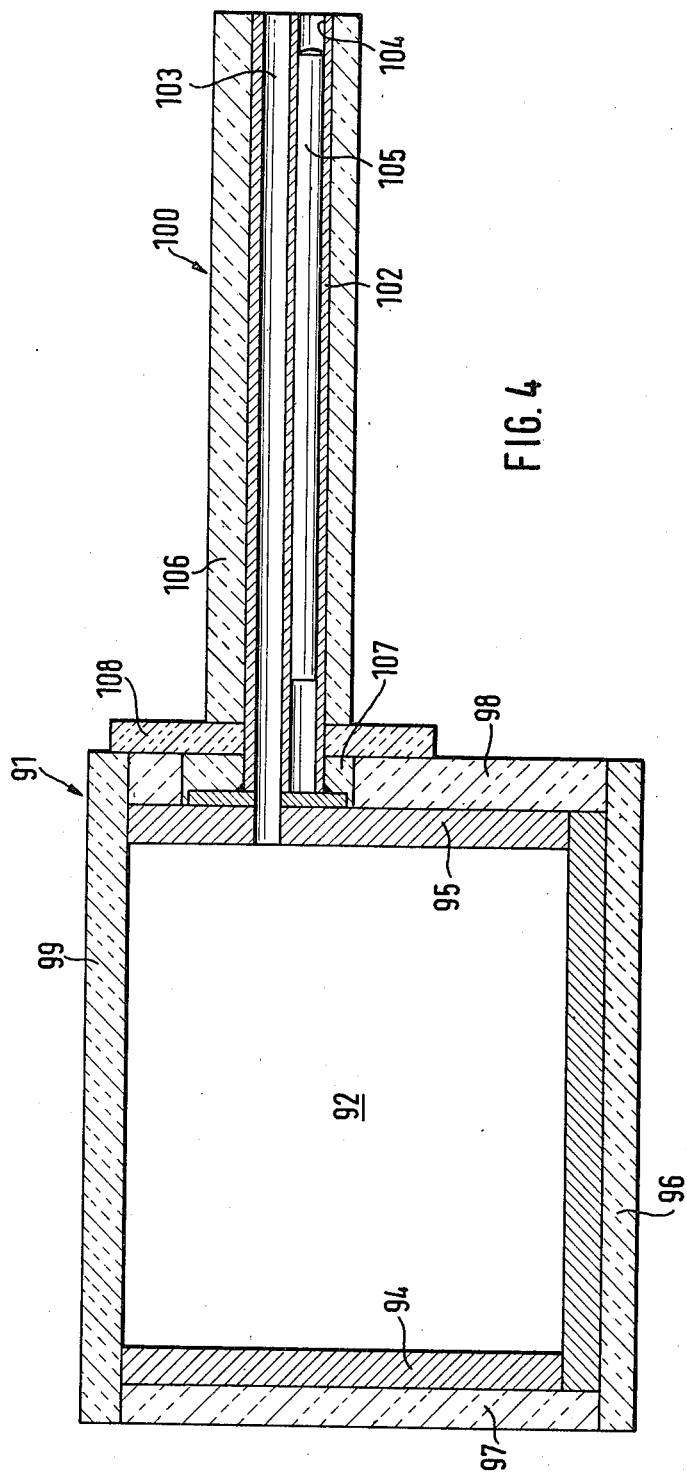
FIG. 4 Vertical section through a stove-type casing modified in comparison with FIG. 1 for the analyzer and the connected probe.

FIG. 4 shows a stove-type casing 91, which surrounds a chamber 92 to accommodate an analyzer as, for example, in FIGS. 2 and 3. The casing 91 has a bottom plate 93 and lateral plates 94 and 95 made in each case of aluminium. Outside the aluminium plates there are insulating plates 96, 97 and 98 respectively, the chamber 92 also having another insulating plate 99 as a top cover plate.

A probe head 100 features an attachment plate 101, which is detachably connected with the aluminium plate 95 by means of screws. Securely connected to the attachment plate 101 is one end of an aluminium body 102 of rectangular cross section, in which there is a through bore 103 for the sampling probe and a bore 104 to accommodate a heating element 105. The body 102 is envelopped by an insulation 106 and there are two further insulating plates 107 and 108 in the zone adjoining the casing 91 and the chamber 92, in order to obtain as complete as insulation as possible, so that there is no cooling down of the extracted gas sample until its concentration has been determined.

What we claim is:

1. Apparatus for extracting a hot gas sample from a chamber and for feeding the sample to an analyzer, in particular for monitoring the content of organic solvents or similar constituents in the air in the chamber, which such solvents or similar constituents represent an explosion hazard or are otherwise harmful when they reach a specific concentration, such apparatus comprising a sampling probe which can be introduced into the chamber through an opening in the chamber wall and is connected outside the chamber with the analyzer, which has a gas filter and a detector, there being a suction pump to draw off the sample through the probe to the analyzer, as well as a heating jacket upstream of the analyzer, wherein the analyzer (2) is located directly at the opening (4) in the chamber wall (5, 6) and is directly connected to the sampling probe (8), the heating jacket (9) surrounds the sampling probe (8) and extends beyond the chamber wall (5, 6) through the chamber-wall opening (4) up to the analyzer (2), the analyzer (2) has a heating apparatus (27) separate from the heating jacket (9) of the sampling probe (8) and the heating jacket (9) and heating apparatus (27) each has its own temperature sensor (14 and 32, respectively) for separate heating and temperature control.

2. Apparatus as in claim 1, wherein the heating apparatus (27) of the analyzer (2) is provided with an insulating jacket (34), which holds the adjacent end of a probe insulating jacket (17) surrounding the heating jacket (9) of the sampling probe (8).

3. Apparatus as in claim 1 or 2, wherein the heating jacket (9) of the sampling probe (8) and the heating apparatus (27) of the analyzer (2) consist in each case of a metal sleeve with axial bores (10, 13 and 28, 31 respectively), into which electrical heating rods (11 and 29, respectively) and the temperature sensors (14 and 32, respectively) are inserted.

4. Apparatus as in claim 1 or 2, wherein the heating jacket (9) for the sampling probe (8) features a radial attachment plate (18) at its end adjacent to the analyzer (2), said attachment plate (18) being detachably connected with the analyzer (2).

5. Apparatus as in claim 1 or 2, wherein a mug-shaped casing (3) is provided to accommodate the analyzer (2), the bottom (44) of which casing (3) has a central hole (45), through which the sampling probe (8) with its surrounding jacket (9, 17) is passed when the analyzer (2) is fitted axially into the casing (3), which also features a projecting flange (46) for attaching it to the chamber wall (5, 6).

* * * * *